United States Patent [19]

Teague

[11] Patent Number: 5,060,657
[45] Date of Patent: Oct. 29, 1991

[54] HEMISPHERICAL NEUROCALOGRAPH

[76] Inventor: Robert A. Teague, 464 Sweetbriar Way, Easley, S.C. 29640

[21] Appl. No.: 541,613
[22] Filed: Jun. 21, 1990
[51] Int. Cl.⁵ .............................................. A61B 5/00
[52] U.S. Cl. .................................... 128/736; 128/742
[58] Field of Search ..................... 128/736, 724, 742; 374/163, 208

[56] References Cited

U.S. PATENT DOCUMENTS

| | | | |
|---|---|---|---|
| 1,648,939 | 11/1927 | Evins | 128/736 |
| 2,161,370 | 6/1939 | Mears | 128/736 |
| 3,626,757 | 10/1967 | Benzinger | 128/736 |
| 3,980,073 | 9/1976 | Shaw, IV | 128/736 |
| 4,043,324 | 8/1977 | Shaw, IV | 128/736 |
| 4,166,451 | 9/1979 | Salera | 128/736 |
| 4,166,451 | 9/1979 | Salera | 128/736 |
| 4,347,854 | 9/1982 | Gosline et al. | 128/736 |
| 4,411,266 | 10/1983 | Cosman | 606/49 |
| 4,595,020 | 6/1986 | Palti | 128/736 |
| 4,854,730 | 8/1989 | Fraden | 128/736 |

Primary Examiner—Francis Jaworski
Assistant Examiner—George Manuel
Attorney, Agent, or Firm—Bailey & Hardaway

[57] ABSTRACT

An improved probe for the measurement of the skin temperature of a living organism is provided. The probe has a probe head constructed of thermally and electrically insulative material and having a generally convex surface for skin contact. The probe head defines a depression in the surface wherein a thermocouple will lie. Additionally, provided is an apparatus using an improved first probe and an improved second probe mounted onto a housing in a mutually symmetrical relationship to measure the temperature differential of bilateral areas of the skin of a living organism.

16 Claims, 7 Drawing Sheets

TO CHART RECORDER

HEMISPHERICAL NEUROCALOGRAPH

BACKGROUND OF THE INVENTION

This invention relates generally to the art of temperature measurement and more particularly to the art of the measurement and display of the temperature differential across bilateral areas of the skin of a living organism in a clinical examination.

The temperature of tissue near the skin surface of a human or animal is known to be higher than normal when the tissue is experiencing spasm, bruising, or other such stress. As a result, the temperature of the adjacent skin surface will also be higher than normal. Therefore, local aberrations in skin surface temperature are sometimes indicative of an inflammation in the underlying tissue. Chiropractors have long utilized this phenomenon in clinical examinations. In particular, neural imbalances resulting from spinal misalignment can be diagnosed based on the differential of the temperature of a skin surface area near the spine on one side and the temperature of the mirror image area on the other side of the spine.

A number of devices have been introduced over the years to assist chiropractors in this temperature differential diagnosis. While these prior art devices have proven successful to some degree, they have significant drawbacks.

The primary shortcoming of the prior art has been in the design of the temperature probes. These probes required the chiropractor to bear against a patient's skin with such pressure that heat-pattern-distorting chafe marks remained after each differential reading. Thus, the accuracy of subsequent readings was negatively affected. A further disadvantage of much of the prior art is that upon completion of the examination, the clinician had no permanent record of the readings. The absence of a chart-type record undoubtedly has caused many nuances of the differential reading to go unnoticed. Additionally, the design of the probes of some prior art devices made cleaning difficult.

Some of the more recent prior art is shown in U.S. Pat. No. 4,166,451 issued to Salera and U.S. Pat. No. 4,347,854 issued to Gosline et al.

SUMMARY OF THE INVENTION

It is thus an object of the invention to provide an improved probe for the measurement of the skin temperature of a living organism.

It is a further and more particular object of the invention to provide a probe for the measurement of the skin temperature of a living organism requiring only slight contact between the probe and the skin surface.

It is also an object of the invention to provide an apparatus for measuring the temperature differential across bilateral areas of the skin of a living organism using improved temperature probes for better accuracy.

Some of these, as well as other, objects are accomplished by a probe having a probe head made of thermally and electrically insulative material and having a generally convex surface for skin contact. The probe head further defines a depression in the surface wherein a thermocouple will lie.

Other objects are accomplished by an apparatus for the measurement of the temperature differential of bilateral areas of the skin of a living organism having an improved first probe and an improved second probe mounted in a mutually symmetrical relationship onto a housing. The difference of voltages produced by thermocouples of the first probe and thermocouples of the second probe is proportional to the temperature differential of the respective skin areas. This differential voltage is amplified if necessary and applied to monitoring means for user interpretation.

Other objects and advantages of the invention will become readily apparent and more fully understood from the following description and drawings.

DETAILED DESCRIPTION

In accordance with the instant invention, it has been found that an improved probe for the measurement of the skin temperature of a living organism may be provided. Furthermore, it has been found that improved probes may be utilized in an apparatus for the measurement of the temperature differential across bilateral areas of the skin of a living organism to secure results not heretofore attainable.

Figure 1:
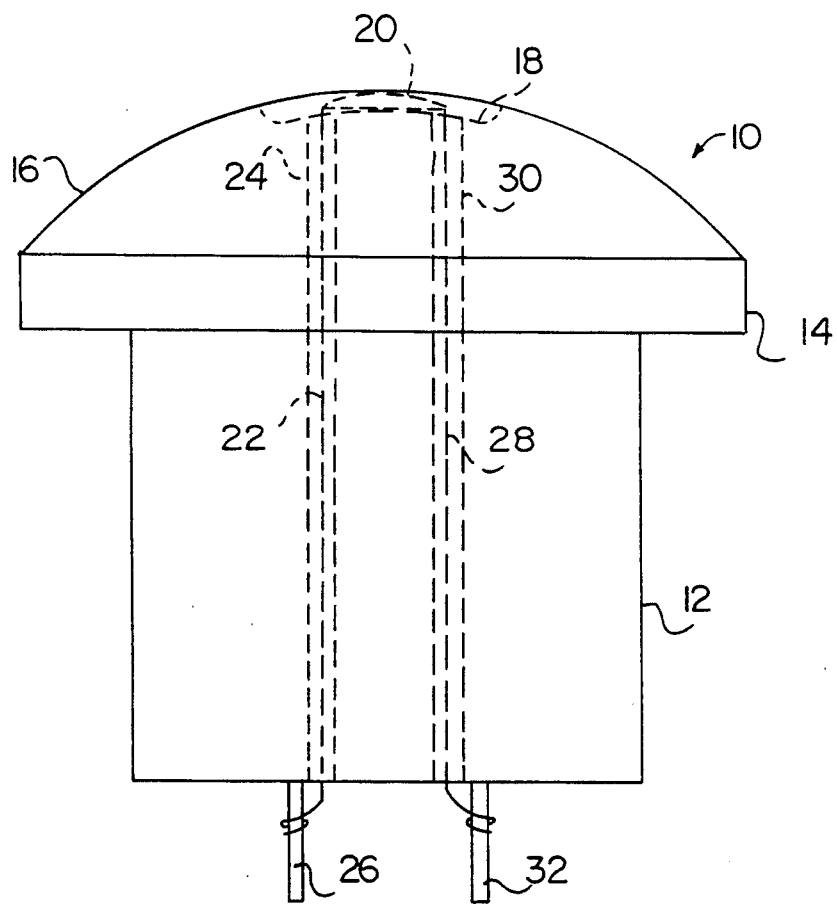
FIG. 1 is an elevation of an improved probe constructed in accordance with the invention illustrating in phantom the situation of the thermocouple of the probe within the depression as well as the thermocouple wires extending longitudinally through the probe.

FIG. 1 illustrates an improved probe 10 in accordance with this invention. Probe 10 is manufactured generally from a thermally and electrically insulative material, such as a polyamide polymer, and comprises a mounting stock 12 and a probe head 14. Probe head 14 has a generally convex skin contact surface 16.

Surface 16 defines a relatively shallow channel-shaped depression 18 wherein a thermocouple 20 is mounted. This arrangement places the thermocouple 20 very near the skin of the organism when surface 16 is lightly touching the skin surface. A plastic filler material (not shown) fills the depression 18 and thereby protects the thermocouple 20 from corrosion or other damage as well as making cleaning of the probe head 14 less difficult. The plastic filler material should preferably be a block epoxy. This gives the target area near the thermocouple 20 a high emissivity. As a result, the thermocouple 20 will be more responsive to heat changes. More accurate probe readings are thereby obtained.

Figure 2:
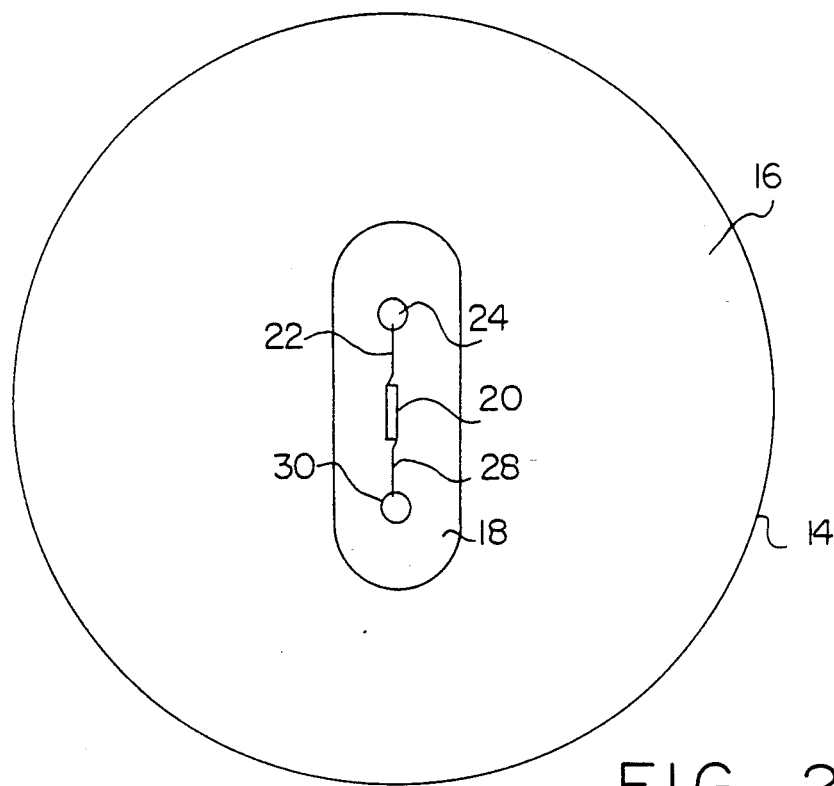
FIG. 2 is a plan view of an improved probe constructed in accordance with the invention showing in detail a thermocouple mounted within a channel-shaped depression.

Thermocouples, like 20, may be formed easily by the contact of two suitable metals. The properties of the thermocouple pair copper and constantan are well known. Specifically, copper-constantan has the highest thermal conductivity and, consequently, the best measurement response time. Copper and constantan is, therefore, the combination preferred for use with the instant invention. Here, copper wire 22 extends through probe 10 within longitudinal aperture 24 and is connected to electrode 26. Similarly, constantan wire 28 extends through probe 10 within aperture 30 and is connected to electrode 32. Electrodes 26 and 32 allow quick hook-up to other circuitry. The formation of thermocouple 20 can be more easily understood with reference to FIG. 2.

Figure 3:
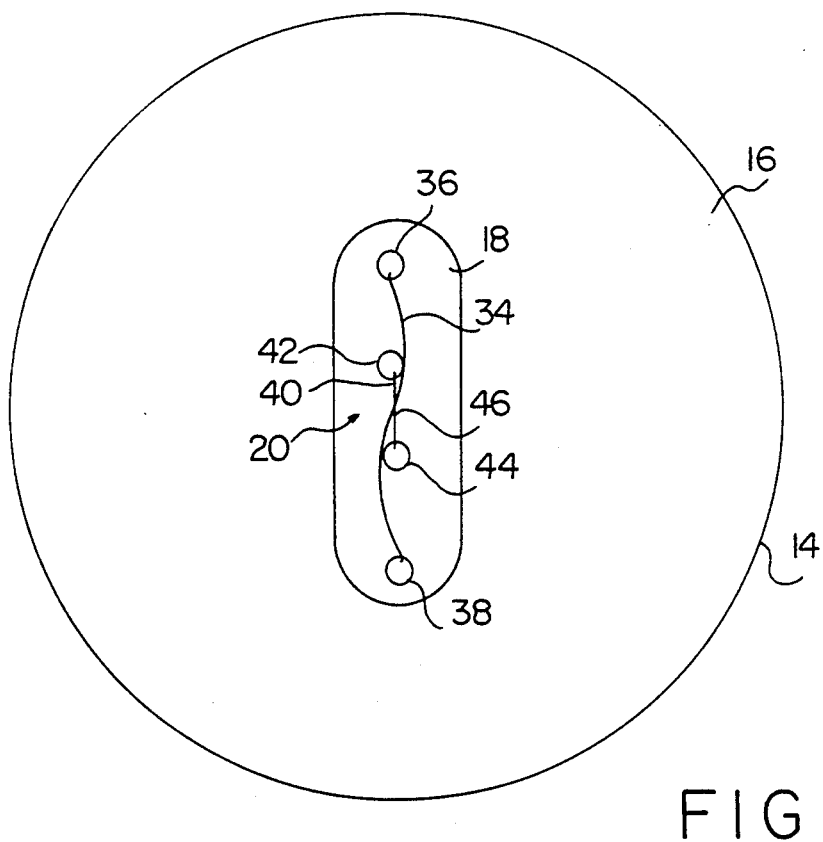
FIGS. 3 through 7 are views similar to FIG. 2 showing other thermocouple embodiments.

Similar thermocouple configurations are shown in FIGS. 3 through 7. FIG. 3 illustrates a four-aperture variation. Copper wire 34 enters depression 18 at aperture 36 and exits depression 18 at aperture 38. Constantan wire 40 proceeds similarly from aperture 42 to aperture 44. The wires 34 and 40 are arranged to mutually cross and contact at point 46, as shown. A thermocouple is thereby formed.

Figure 4:
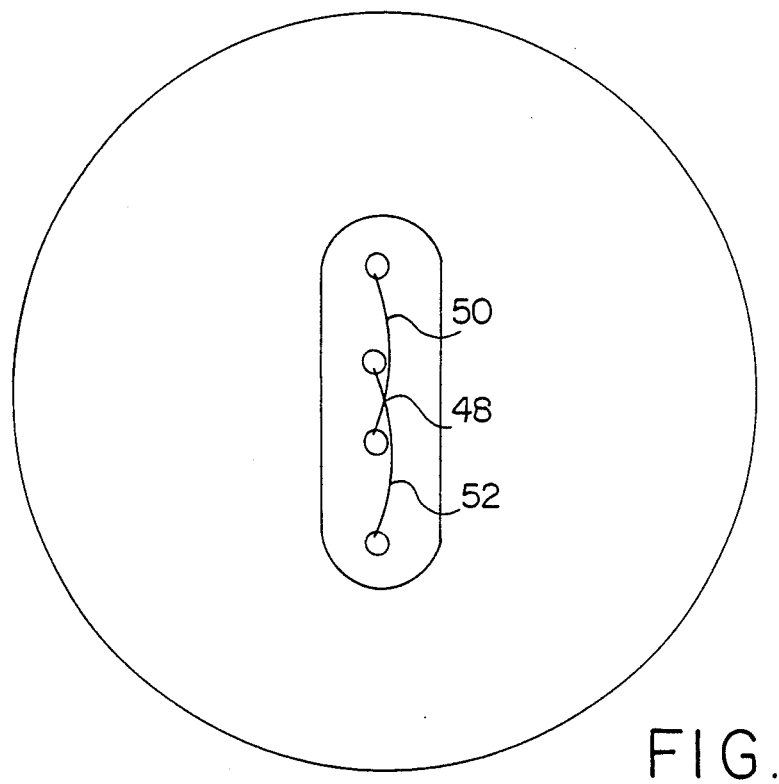

The thermocouple in FIG. 4 is formed at contact point 48 by the mutually crossing contact of copper wire 50 with constantan wire 52.

Figure 5:
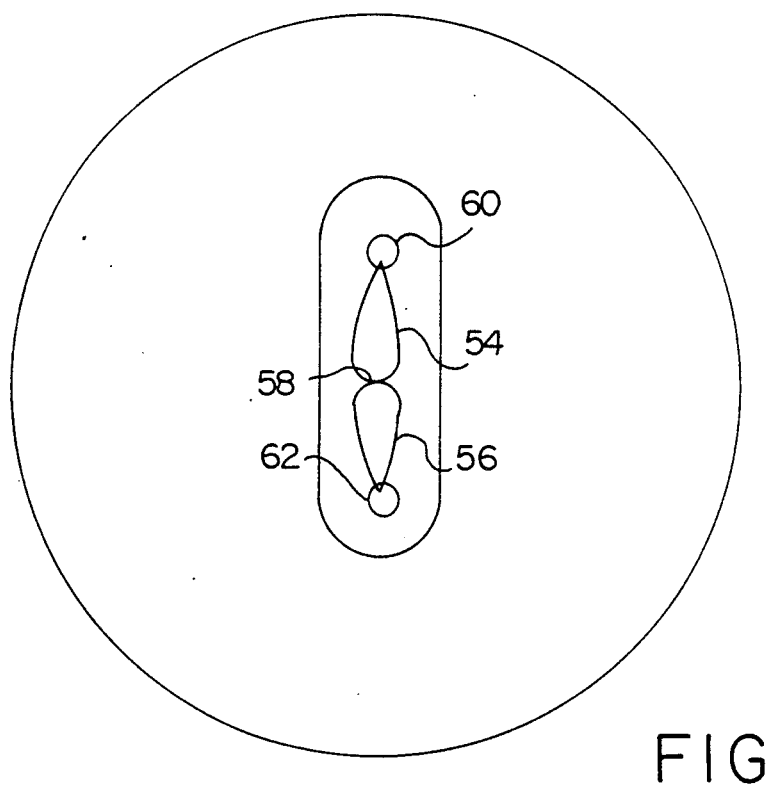

The thermocouple of FIG. 5 is formed by the mutually linking contact of copper wire loop 54 and constantan wire loop 56 at contact point 58 Note that this configuration requires only two apertures 60 and 62.

Figure 6:
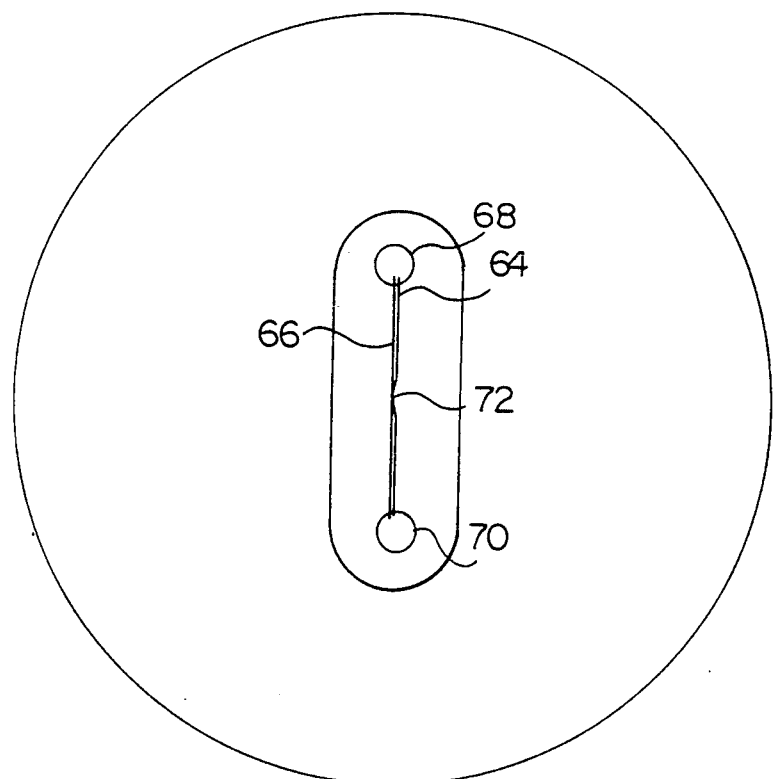

Another two-aperture configuration is shown in FIG. 6. Copper wire 64 and constantan wire 66 are parallel to each other and extend longitudinally from aperture 68 to aperture 70. Wires 64 and 66 are uninsulated at tangent contact point 72 only.

Figure 7:
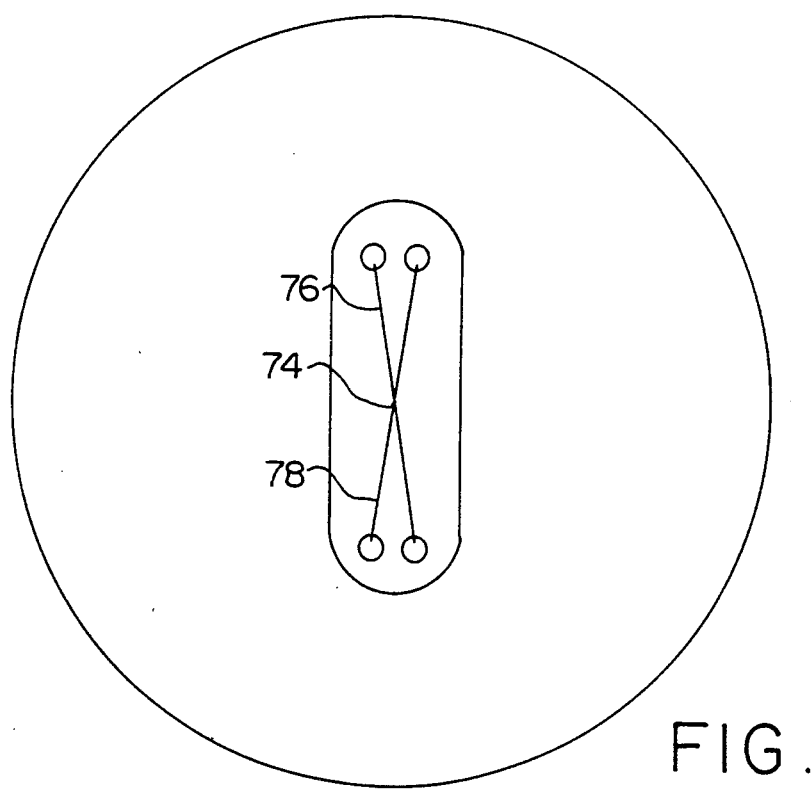

FIG. 7 illustrates a four-aperture configuration whereby the thermocouple is formed by the contact at point 74 of copper wire 76 with constantan wire 78.

Figure 8:
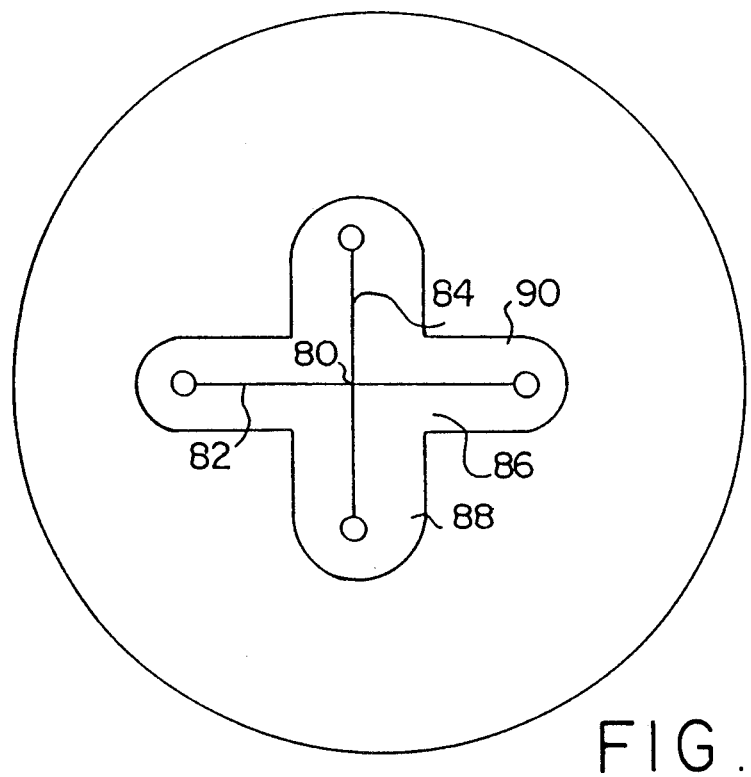
FIG. 8 is a plan view of an improved probe constructed in accordance with the invention showing in detail a thermocouple mounted within a cross-channel depression.
Figure 9:
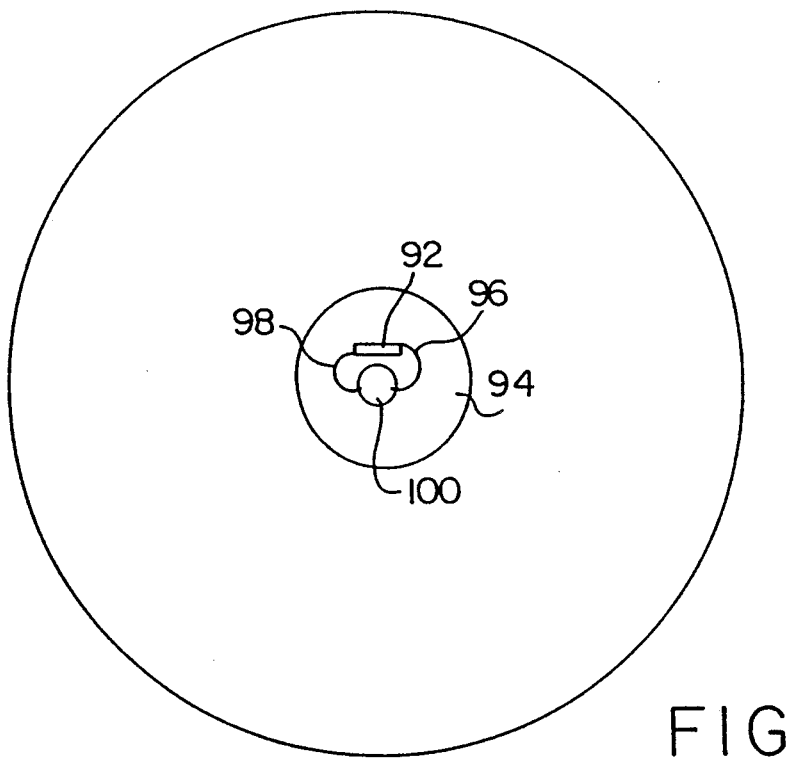
FIG. 9 is a plan view of an improved probe constructed in accordance with the invention showing in detail a thermocouple mounted within a dimple-shaped depression.

The probe depression may take on any number of alternative configurations, two of which are illustrated in FIG. 8 and 9. In FIG. 8, a thermocouple is formed at the intersection (at point 80) of constantan wire 82 with copper wire 84. Note that here the depression 86 is of cross-channel formation. That is, depression 86 is formed by the mutual crossing of channels 88 and 90. Channels 88 and 90 are of approximately equal depth.

In FIG. 9, thermocouple 92 is formed within dimple-shaped depression 94 by the contact of copper wire 96 with constantan wire 98. Wires 96 and 98 are uninsulated only at the contact point since they emerge from a single aperture 100.

With any of these thermocouple configurations, copper-constantan contact may be maintained by wire-wrapping, soldering, gluing, or any combination thereof. Also, the probes may have more than one thermocouple. One thermocouple per probe has been illustrated for the sake of clarity only.

Figure 10:
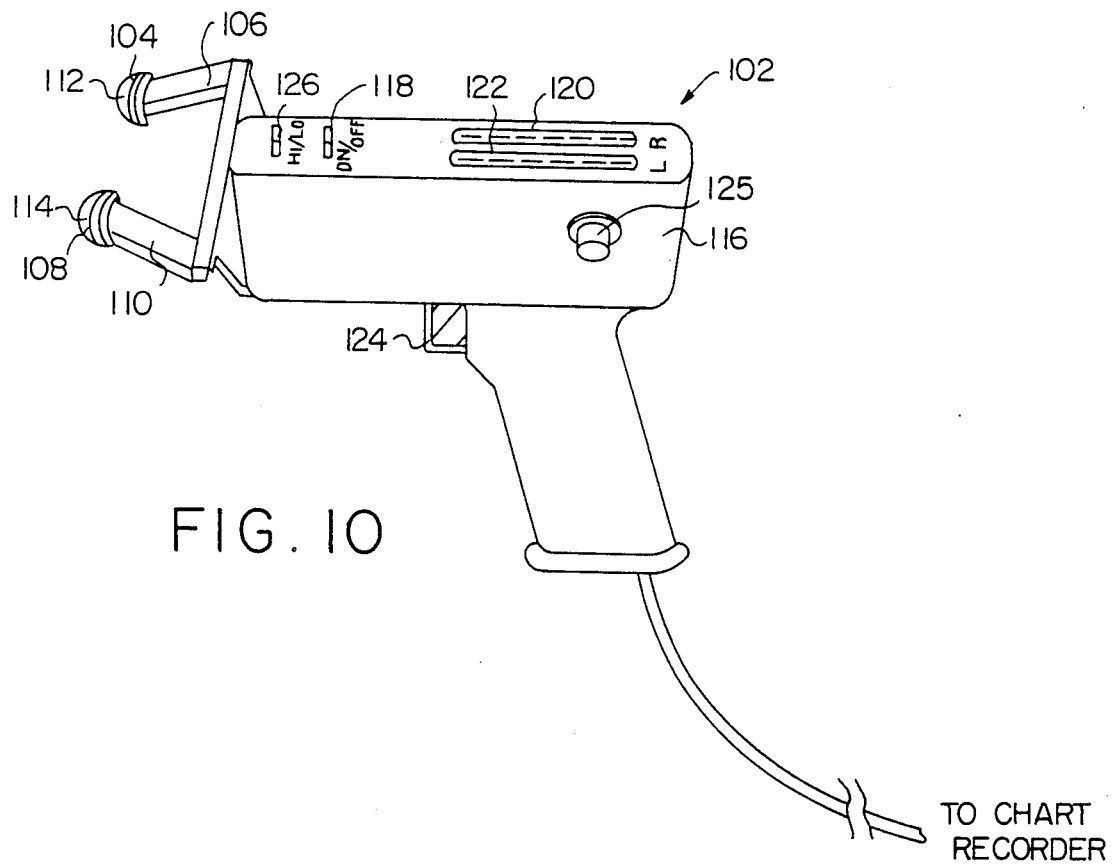
FIG. 10 is a perspective view of the neurocalograph apparatus of the invention.

Many of the advantages of the improved probes discussed above can be realized when employed in a neurocalograph. FIG. 10 illustrates a neurocalograph 102, which is an apparatus primarily used by chiropractors for measuring the temperature differential of bilateral skin areas on either side of the human spine (see FIG. 11). Neurocalograph 102 has a first improved probe 104 mounted on first mounting arm 106 and a second improved probe 108 mounted on a second mounting arm 110. Probes 104 and 108 are of the type previously described and have thermocouples 112 and 114, respectively. Mounting arms 106 and 110 are attached in a mutually symmetrical relationship to a pistol-grip housing 116. An on/off switch 118 is provided so that the user can easily activate the neurocalograph 102. Display means, such as light emitting diode (LED) bars 120 and 122 and a separately housed chart recorder (not shown), are provided. A chart recorder allows the clinician to concentrate on the movement of the neurocalograph and not the reading as it is being taken. Thus, improved accuracy is realized. The chart recorder paper is advanced as desired by trigger switch 124. The positioning of switch 124 as a trigger is preferred over other possible designs because overall balance is disrupted minimally by the force of the user's finger in this way. Knob 125 is provided so that the user can adjust the chart recorder pen to the zero position before each use. For optimum versatility, the chart recorder is adapted to be capable of being adjusted to numerous chart speeds and sensitivity levels. Contained within housing 116 is circuitry, including a differential input operational amplifier (op-amp). The op-amp has a plurality of gain values, which are selectible by gain switch 126.

Figure 11:
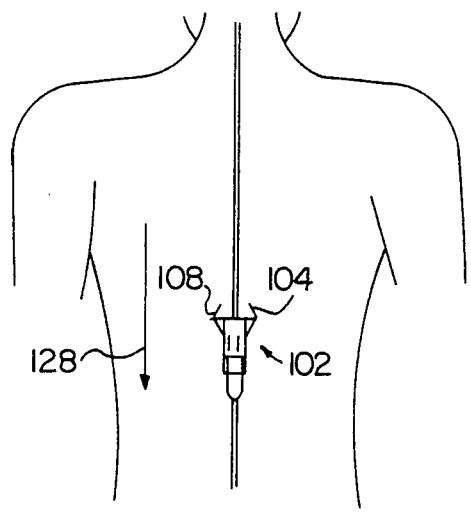
FIG. 11 is a view illustrating the usage of the neurocalograph of the invention in a clinical examination.
Figure 12:
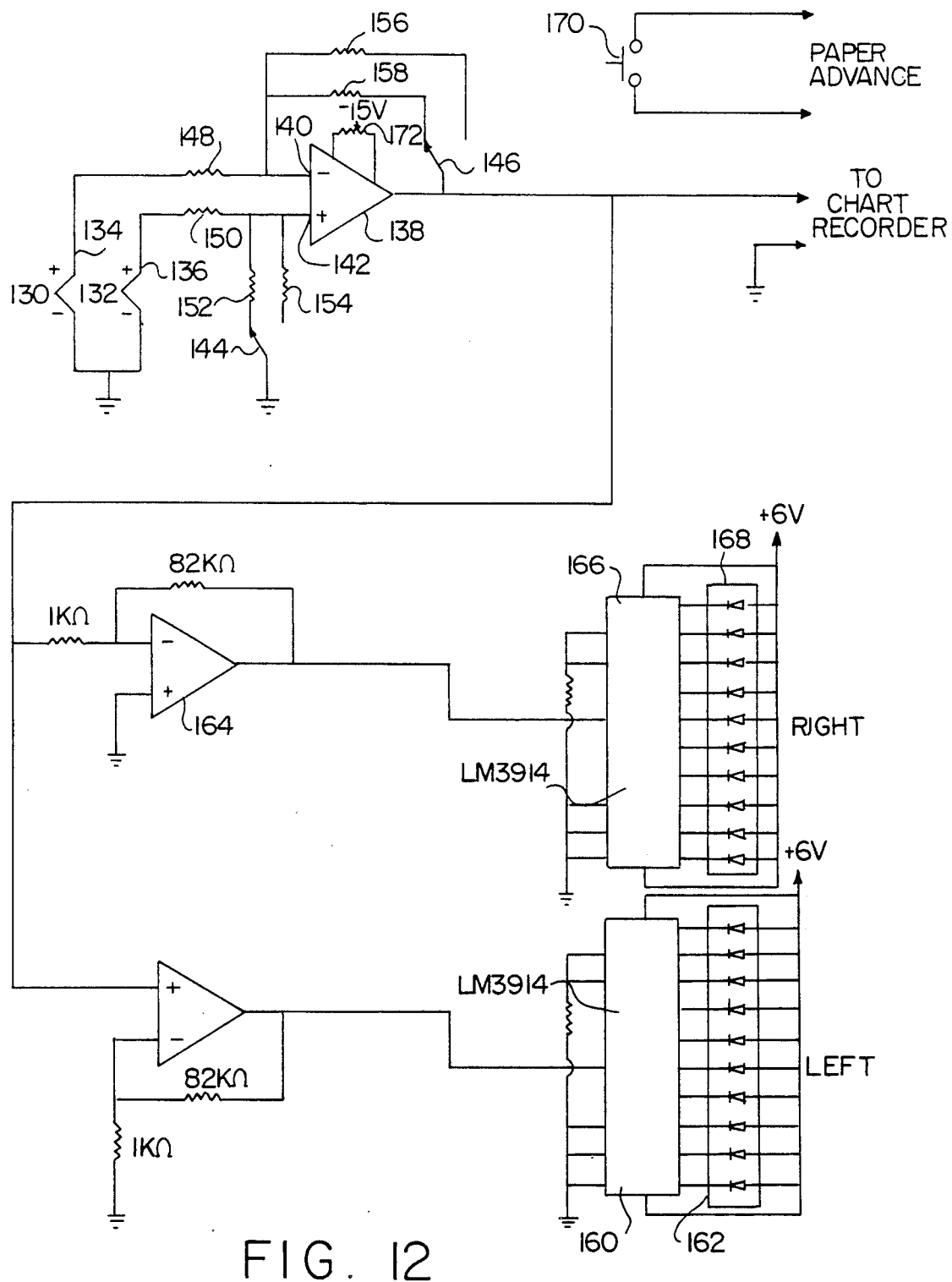
FIG. 12 is a schematic of the electrical circuitry of the neurocalograph of the invention.

The operation of neurocalograph 102 will now be explained with reference to FIGS. 10, 11 and 12. As the probes 104 and 108 of neurocalograph 102 are applied lightly to bilateral skin areas across the spine, voltages will be produced at thermocouples 112 and 114 (shown as 130 and 132 of FIG. 12) proportional to the temperature of the respective adjacent areas. Because thermocouples 130 and 132 are both grounded, they are in mutual nodal oppositely polarized electrical communication. Therefore, the voltage as measured from the positive lead 134 of thermocouple 130 to the positive lead 136 of thermocouple 132 is the difference of the voltages across each thermocouple individually. This voltage difference is usually too small to be useful unless amplified. Therefore, a differential amplifier 138 is provided having an inverting input 140 and a non-inverting input 142.

Means are provided such that thermocouple 130 is in electrical communication with input 140 and thermocouple 132 is in electrical communication with input 142. As one skilled in the art will recognize, switches 144 and 146 (actually one double-pole double-throw switch and shown as 126 in FIG. 10) allow the user to select between two gains. Normally, readings should be taken in the low gain position. However, the low gain position will occasionally yield an insufficient reading, in which case the high gain position is required. For example, patients on medication will sometimes show a masked signal. A gain of twenty has been found suitable for the low gain mode and a gain of twenty-eight has been found suitable for the high gain mode. To achieve these gains, the resistors 148, 150, 152, 154, 156 and 158 should have values in the kilo-ohm range. The output of amplifier 138 will either be positive or negative, depending on which of its inputs (140 or 142) has the higher input voltage. One skilled in the art will recognize that a positive output from amplifier 138 will be processed by chip 160 to light a number of LED's within display 162 (shown as 122 of FIG. 11) proportional to the magnitude of the differential voltage. A negative output from amplifier 138 will be inverted by amplifier 164 and similarly processed by chip 166 and displayed on 168 (shown as 120 of FIG. 10). In this way the user knows not only which bilateral skin area is at a higher temperature, but the magnitude of the temperature difference as well. As the neurocalograph 102 is drawn down the patient's neck and back (as shown by arrow 128 of FIG. 11), the clinician can fully diagnose the patient's spinal misalignment neural imbalance. The improved design of probes 104 and 108 allows this reading to be made with only light pressure, eliminating the heat pattern distorting chafe makes caused by prior art devices. This ensures that successive readings are as accurate as the first. The output of amplifier 138 is also fed to the chart recorder, giving the user a permanent record of the examination readings for later, more detailed analyses. Trigger switch 124 and knob 125 of FIG. 10 are illustrated schematically as switch 170 and potentiometer 172, respectively. It should be noted that a chart recorder with a built-in amplifier may be used, eliminating the need for amplifier 138.

It is thus apparent that an improved probe for the measurement of the skin temperature of a living organism has been provided. It is also apparent that an apparatus using improved probes to measure the temperature differential across bilateral areas of the skin of a living organism has been provided. As many variations will be apparent from a reading of the above description, such variations are embodied within the spirit and scope of this invention as defined by the following appended claims.

That which is claimed is:

1. A probe for the measurement of the skin temperature of a living organism comprising:
    a thermally and electrically insulative probe head having a generally convex skin contact surface, said head defining a depression in said surface; and
    a thermocouple comprising the contact of two suitable metal wires attached within said depression, said depression of a depth such that said thermocouple will be in close proximity with the skin of said organism when said probe head is in contact with said skin.

2. The probe according to claim 1 wherein said probe head comprises a polyamide polymer.

3. The probe according to claim 1 wherein said thermocouple comprises the contact of copper wire with constantan wire.

4. The apparatus according to claim 1 wherein a plastic filler material fills said depression to protect said thermocouple.

5. The apparatus according to claim 4 wherein said plastic filler material is a black epoxy.

6. The probe according to claim 1 wherein said probe head contains a depression comprising intersecting channels of approximately equal depth, each said channel containing one wire extending longitudinally therein, said wires forming a thermocouple at the intersection of said channels.

7. The probe according to claim 1 wherein said thermocouple is formed by the tangent contact of parallel wires extending longitudinally within said depression.

8. The probe according to claim 1 wherein said thermocouple is formed by the contact of wires mutually crossing within said depression.

9. The probe head according to claim 1 wherein a loop is formed in each said wire, said loops mutually linking within said depression such that a thermocouple is formed by the contact of said loops with each other.

10. An apparatus for the measurement of the temperature differential of bilateral areas of the skin of a living organism comprising:
    a first probe comprising a thermally and electrically insulative probe head having a generally convex skin contact surface and defining a depression in said surface;
    a second probe comprising a thermally and electrically insulative probe head having a generally convex skin contact surface and defining a depression in said surface;
    a thermocouple formed within each said depression of a size such that said thermocouple will be in close proximity with the skin of said organism when said probe head is in contact with said skin, each said thermocouple producing a voltage proportional to the temperature of said skin area;
    a housing onto which said probes are attached in a mutually symmetrical relationship whereby said probes can contact said bilateral areas;
    a differential amplifier having an inverting input and a non-inverting input;
    means providing electrical communication between the thermocouple of the first probe and said inverting input and further providing electrical communication between the thermocouple of the second probe and said non-inverting input whereby said amplifier generates an output signal proportional to said temperature differential; and,
    display means in electrical communication with said differential amplifier and said thermocouples such that said temperature differential can be monitored and interpreted by the user.

11. The apparatus of claim 10 wherein said display means is a light emitting diode display attached on said housing.

12. The apparatus of claim 10 wherein said display means is a chart recorder.

13. The apparatus of claim 10 wherein said display comprises a light emitting diode display attached on said housing and further comprises a chart recorder.

14. The apparatus of claim 10 further comprising switching means for switching said differential amplifier to have multiple gain values whereby the user of the apparatus can select a particular value depending upon the magnitude of the difference between said inverting input and said non-inverting input of said amplifier.

15. An apparatus for the measurement of the temperature differential of bilateral areas of the skin of a living organism comprising:
    a first probe comprising a thermally and electrically insulative probe head having a generally convex skin contact surface and defining a depression in said surface;
    a second probe comprising a thermally and electrically insulative probe head having a generally convex skin contact surface and defining a depression in said surface;
    a thermocouple formed within each said depression of a size such that said thermocouple will be in close proximity with the skin of said organism when said probe head is in contact with said skin, each said thermocouple producing a voltage proportional to the temperature of said skin area;
    a housing onto which said probes are attached in a mutually symmetrical relationship whereby said probes can contact said bilateral areas;
    means providing electrical communication between the thermocouple of said first head and the thermocouple of said second head such that a voltage output equal to the difference of the individual probe head voltages and thereby proportional to the temperature differential of said bilateral areas is generated; and display means in electrical communication with said thermocouples such that said temperature differential can be monitored and interpreted by the user.

16. The apparatus of claim 15 wherein said display means is a chart recorder with an integral input amplifier.

* * * * *